(12) United States Patent
Webb et al.

(10) Patent No.: US 10,446,268 B2
(45) Date of Patent: Oct. 15, 2019

(54) SYSTEMS AND METHODS FOR MAINTAINING AND PROCESSING PROPRIETARY OR SENSITIVE DATA IN A CLOUD-HYBRID APPLICATION ENVIRONMENT

(71) Applicant: OPTUM, INC., Minnetonka, MN (US)

(72) Inventors: Joseph Arvel Webb, La Verkin, UT (US); David Bennion, Saratoga Springs, UT (US); Eric Kemp McCune, Salt Lake City, UT (US); Brent Udell Smith, Farmington, UT (US)

(73) Assignee: OPTUM, INC., Minnetonka, MN (US)

(*) Notice: Subject to any disclaimer, the term of this patent is extended or adjusted under 35 U.S.C. 154(b) by 866 days.

(21) Appl. No.: 14/829,168

(22) Filed: Aug. 18, 2015

(65) Prior Publication Data
US 2016/0048645 A1 Feb. 18, 2016

Related U.S. Application Data

(60) Provisional application No. 62/038,637, filed on Aug. 18, 2014.

(51) Int. Cl.
*G16H 40/20* (2018.01)
*G06F 19/00* (2018.01)
(Continued)

(52) U.S. Cl.
CPC ............ *G16H 40/20* (2018.01); *G06F 16/25* (2019.01); *G06F 19/324* (2013.01); *G06F 21/6245* (2013.01)

(58) Field of Classification Search
CPC ........ G06Q 50/22; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70;
(Continued)

(56) References Cited

U.S. PATENT DOCUMENTS

| | | | | |
|---|---|---|---|---|
| 2013/0232246 A1* | 9/2013 | Miller | ........................ | G06F 8/71 709/222 |
| 2013/0263088 A1* | 10/2013 | Hoff | ......................... | G06F 8/61 717/121 |
| 2014/0189865 A1* | 7/2014 | Abuelsaad | .............. | G06F 21/55 726/23 |

\* cited by examiner

*Primary Examiner* — Joy Chng
(74) *Attorney, Agent, or Firm* — Seyfarth Shaw LLP; Brian Michaelis (57) ABSTRACT

Systems, methods, and apparatuses for maintaining and processing proprietary or sensitive data using an application implemented in a split/hybrid-cloud system are described. The split/hybrid system utilizes cloud and local platforms, while complying with customer security concerns and HIPAA security standards. Configuration of the application occurs in a cloud platform whereas processing of proprietary or sensitive data occurs within a customer's local computing environment. The customer may create their own unique application configuration that is stored in the cloud platform and that is delivered back to the customer as a package that includes both the unique application configuration as well as general application configuration requirements. The customer may implement the package within one or more local computing environments while managing the application from a single site that is separated from proprietary or sensitive data.

20 Claims, 4 Drawing Sheets

(51) Int. Cl.
*G06F 21/62* (2013.01)
*G06F 16/25* (2019.01)

(58) Field of Classification Search
CPC ........ G16H 20/90; G16H 30/00; G16H 40/00;
G16H 40/20; G16H 40/40; G16H 40/60;
G16H 40/63; G16H 40/67; G16H 50/00;
G16H 70/00; G16H 70/20; G16H 70/40;
G16H 70/60; G16H 80/00; G06F
21/6245; G06F 19/324; G06F 16/25
USPC ........................................................ 705/2–3
See application file for complete search history.

SYSTEMS AND METHODS FOR MAINTAINING AND PROCESSING PROPRIETARY OR SENSITIVE DATA IN A CLOUD-HYBRID APPLICATION ENVIRONMENT

CROSS-REFERENCE TO RELATED APPLICATION DATA

This application claims priority to U.S. Provisional Patent Application Ser. No. 62/038,637, which is incorporated herein by reference in its entirety.

FIELD OF TECHNOLOGY

The present disclosure relates generally to computing environments, and more particularly to hybrid computing environments.

BACKGROUND

Healthcare providers typically utilize locally maintained computing platforms to manage customer records. Utilization of locally maintained computer platforms is primarily dictated by customer concerns regarding privacy and the healthcare providers' duty to comply with industry and government standards, such as the Health Insurance Portability and Accountability Act ("HIPAA"). However, updates to the locally maintained platforms are disruptive to systems with high-availability requirements. Moreover, local/on premise platforms that keep proprietary data away from cloud environments limit technical support, understanding of platform/application usage patterns, and present testing challenges for cloud-based service providers.

To overcome the disruption caused by locally maintained platforms, healthcare providers often find it desirable to utilize cloud platforms. However, healthcare customers are concerned about privacy provided by cloud platforms. Furthermore, processing of proprietary or sensitive information cannot be performed using cloud-based platforms due to data security concerns that violate customer trust and HIPAA. The healthcare providers' desire to keep certain information away from cloud environments limits localized configuration management, and introduces complexity and deployment problems into cloud based systems.

SUMMARY

The present disclosure generally provides systems, methods, and apparatuses for maintaining and processing proprietary or sensitive data using an application implemented in a specially configured split/hybrid-cloud system. The split/hybrid system, which utilizes both a cloud platform and a local platform, complies with customer security concerns and government privacy standards. The split/hybrid system provides localized processing and retention of proprietary or sensitive data and cloud centralized configuration and content management. In the event of damage to or loss of data in the local execution environment, the present disclosure does not result in a loss to configuration content, and vice versa.

Integrated content may be sourced by a third party vendor and provided to healthcare providers en masse. For example, the third party vendor may provide general configuration rules/logic and datasets for implementation of a core application. The healthcare provider has the ability to create their own configuration logic/rules within the cloud platform, that are ultimately delivered back to the healthcare provider as a configuration capsule. For example, the healthcare provider may provide the cloud with specific application configuration rules/logic, which are delivered back to the healthcare provider's local execution environment as a configuration capsule including general application configuration rules/logic along with the healthcare provider specific configuration rules/logic. Thus, the present disclosure provides a content and logic capsule, which the healthcare provider can deliver to one or more local computing environments, but which can be managed from a single site that is separated from proprietary or sensitive data.

As noted above, the present disclosure provides configuration capsules that are tailored to individual healthcare provider needs. This allows for simple switching between multiple configuration capsules to allow for easy testing of new versions and rollback to prior versions of the core application. This is beneficial regarding version management of configuration data.

The present disclosure may be implemented within Integrated Claims Processing ("ICP") Claims Editing products/core applications such as Claims Manager and Claims Edit System products/core application by Optum Corporation of Eden Prairie, Minn. The present disclosure may also be implemented to comply with Analytic Common Capability (ACC), which supports multiple products, and with HIPAA, Electronic Data Exchange ("EDE"), and Electronic Medical Records ("EMR") platforms.

BRIEF DESCRIPTION OF THE DRAWINGS

Embodiments of devices, systems, and methods are illustrated in the figures of the accompanying drawings which are meant to be exemplary and non-limiting, in which like references are intended to refer to like or corresponding parts, and in which.

DETAILED DESCRIPTION

The detailed description of aspects of the present disclosure set forth herein makes reference to the accompanying drawings and pictures, which show various embodiments by way of illustration. While these various embodiments are described in sufficient detail to enable those skilled in the art to practice the disclosure, it should be understood that other embodiments may be realized and that logical and physical changes may be made without departing from the spirit and scope of the disclosure. Thus, the detailed description herein is presented for purposes of illustration only and not of limitation. For example, the steps recited in any of the method or process descriptions may be executed in order other than as presented and are not limited to the order presented. Moreover, references to a singular embodiment may include plural embodiments, and references to more than one component may include a singular embodiment.

The present disclosure generally relates to specially configured systems, methods, and apparatuses for maintaining and processing proprietary or sensitive data in an improved computer/network using an application implemented in a split/hybrid-cloud system. An application/program is implemented in a split/hybrid system in a manner that complies with healthcare industry privacy standards while improving computation efficiency. Configuration of the application occurs in a cloud platform/environment, whereas processing and retention of proprietary or sensitive data occurs within a healthcare provider's local, secure computing environment. The healthcare provider may create their own unique application configuration logic/rules that are stored in the cloud platform and that are delivered back to the healthcare provider as a configuration capsule that includes both the unique configuration logic/rules as well as general application configuration logic/rules. The configuration capsule may be implemented within one or more secure local computing environments of the healthcare provider while management of the application occurs at a single site separated from proprietary or sensitive data stored in the local computing environment(s).

Figure 1:
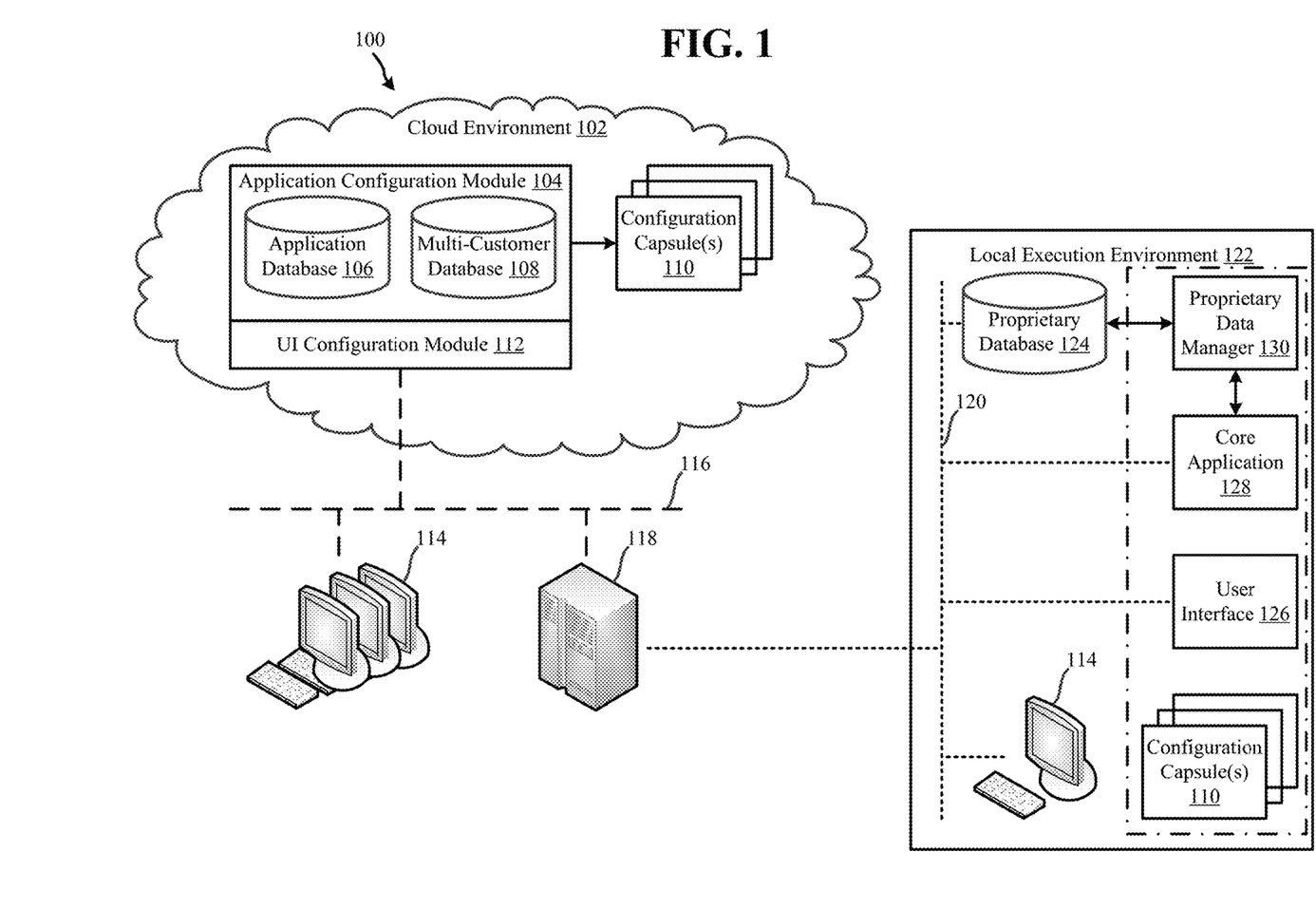
FIG. 1 illustrates a specially configured cloud-hybrid system for secure processing and maintaining proprietary or sensitive data according to the present disclosure.

Referring to FIG. 1, a specially configured cloud-hybrid system 100 for processing and maintaining proprietary or sensitive data is described. The system 100 includes a cloud environment 102, which may be provided by a vendor such as AMAZON®, GOOGLE®, APPLE®, MICROSOFT®, and OPTUM®, for example. The cloud environment 102 includes an application configuration module 104, within which are an application database 106 and a multi-customer database 108. The data stored within the application database 106 may be supplied by the application's creator while the data stored within the multi-customer database 108 is provided by individual healthcare providers. The application database 106 includes rules/logic governing general configuration of the application. For example, the rules/logic contained within the application database 106 may be provided by Optum Corporation of Eden Prairie, Minn. The application database 106 may also include data or datasets that specify or comply with requirements of different entities (e.g., federal and local governments) regarding healthcare management. For example, the data or datasets may provide instructions regarding how healthcare claims should be processed. The multi-customer database 108 includes healthcare provider specific application configuration logic/rules. These healthcare provider logic/rules may be proprietary to the healthcare provider that generated them. Thus, the multi-customer database 108 may be configured to allow healthcare providers to only access the logic/rules they generated, thereby maintaining secrecy from unauthorized access by others including other healthcare providers. Each healthcare provider's configuration logic/rules may be a line item within the multi-customer database 108.

A configuration capsule 110 is generated for a healthcare provider using data stored within the application database 106 and the multi-customer database 108. The configuration capsule 110 contains all the elements needed to define and support rule behavior by the application. Encapsulation options include packaging existing binary (engine) and string (rules, data) elements for import, or delivering them in an executable form via an H2 (Java SQL) or similar database. The configuration capsule 110 is built to facilitate system efficiency and security by including generalized application configuration rules/logic and data/datasets from the application database 106 and customized application configuration rules/logic, specific to and provided by the healthcare provider that will receive the capsule, from the multi-customer database 108. Upon generation, the configuration capsule 110 is communicated from the cloud environment 102 to the relevant healthcare provider's local execution environment 122 (discussed in detail below). For example, the configuration capsule 110 may be pushed from the cloud environment 102 to the local execution environment 122 by the application creator. In another example, the configuration capsule 110 may be pulled from the cloud environment 102 to the local execution environment 122 by the customer. Prior to delivery to the local execution environment, the configuration capsule 110 may be encrypted by means known to those skilled in the art to protect proprietary data contained therein from unauthorized access.

The configuration capsule 110 can be altered/modified and should be fluid (i.e., change over time) to comply with updated and revised industry standards and rules changes. Thus, more than one configuration capsule 110 may be generated for a single healthcare provider. For example, a configuration capsule 110 may be generated at a certain time and another configuration capsule 110 may be generated for the same healthcare provider at a subsequent time. This may occur when an update for the application is available (i.e., new rules/logic and/or data/datasets have been provided to the application database 106 subsequent to generation of the first configuration capsule 110). A new configuration capsule 110 may be automatically generated without healthcare provider intervention upon new rules/logic and/or data/datasets being provided to the application and/or multi-customer databases 106, 108.

Previously generated configuration capsules 110 may be stored within the cloud environment 102 and/or the local execution environment 122 (described in detail below). This allows for easy switching between versions of the configuration capsules 110. In other words, this allows for roll back to older versions of the application to occur seamlessly, without necessarily needing support or intervention from the application's creator.

Each configuration capsule 110 may contain all of the datasets present in the application database 106 when the configuration capsule 110 is generated. However, not all of the datasets need be utilized in the local execution environment 122 (described in detail below) of the healthcare provider. Since each configuration capsule 110 incorporates logic/rules from both the application and multi-customer databases 106, 108, each configuration capsule 110 may contain both nonproprietary and proprietary logic/rules generated by third parties (e.g., the application creator) and the customer.

The cloud environment 102 also includes a user interface ("UI") configuration module 112. The UI configuration module 112 is a rich customization environment that allows healthcare providers to tailor their UIs in a variety of ways. Configuration preferences (i.e., rules/logic) may be communicated from a healthcare provider to the UI configuration module 112 using a computing device 114. The computing device 114 may be a desktop, laptop, tablet, personal digital assistant, smartphone, or like device capable of transmitting configuration preference rules/logic to the UI configuration module 112. Communication between the UI communication module 112 and the computing device 114 occurs via a communication pathway 116. The communication pathway 116 may be the Internet, in which case the computing device 114 may be connected to the communication pathway 116 via wired or wireless technologies known in the art.

The cloud environment 102 is in communication with a demilitarized zone ("DMZ") 118 via the communication pathway, which as described above may be the Internet. The DMZ 118 is a subnetwork or perimeter network of the healthcare provider local execution environment 122 (described in detail below) that provides an interface between the local execution environment 122 and untrusted communications coming from the communication pathway 116. Thus, the DMZ 118 provides an additional layer of security to the healthcare provider's local area network ("LAN") or intra-net 120.

The healthcare provider's local execution environment 122 includes a computing device 114, a proprietary database 124, a user interface 126, a core application 128, and a proprietary data manager 130. The local execution environment 122 also includes the configuration capsule(s) 110, specifically configured/tailored to the healthcare provider's preferences. Previously generated configuration capsules 110 may be stored within the local execution environment 122 to allow for easy switching between versions of the configuration capsules 110. In other words, this allows for roll back to older versions of the application to occur seamlessly, without necessarily needing support or intervention from the application's creator.

The computing device 114 is configured to interact with the user interface 126 of the core application 128. The computing device 114 may be a desktop, laptop, tablet, personal digital assistant, smartphone, or like device. Further, the computing device 114 may include a web browser that allows the computing device 114 to communication with the user interface 126 via the intra-net 120.

The user interface 126 is specially configured to provide rule life cycle management. Regarding rule life cycle management, rules for validity checking and clinical content accuracy analysis are delivered on a periodic basis as the underlying knowledge base updates. The user interface 126 has a selection function, such as a drop down function, whereby a user sets rules to be used for claim analysis by assigning statuses (e.g., test, production, disable). This results in the user of the user interface 126 having control over the action of each rule.

The user interface 126 is also specially configured to provide ruleset and route management. Rules may be grouped into "rulesets" based on attributes assigned to each rule. This consolidation of the rules into rulesets greatly simplifies the ruleset maintenance required of users because, as new rules are added, they are automatically inserted into the appropriate rulesets based on the rule attributes assigned to each ruleset. In addition, the user interface 126 provides the user with the ability to create "exceptions" that either suppress rules that would normally be included (based on the rule attributes) or add rules to the ruleset that would normally be excluded. Claims are "routed" to a particular defined ruleset based on "claim matching" conditions specified by the user (via the user interface 126) and associated with the ruleset. A claim matching conditional expression may also be associated with each "exception" that modifies the initial ruleset.

Additionally, the user interface 126 is specially configured to provide rule creation. A user may create their own claim analysis rules via tools provided by the user interface 126. These rules are segregated from the system rules that are delivered to the local execution environment 122 via the configuration capsule(s) 110.

The core application 128 may perform, in compliance with the data of the configuration capsule 110, clinical content editing (e.g., healthcare claims validity analysis) and/or analysis of structural correctness of data transmissions, for example. The core application 128 executes rules defined by subject matter expert users of the core application 128, for example. These rules may have the ability to compare and change data elements provided for by defined meta-data. Additionally, the core application 128 may support mathematical and SQL based calculations, for example.

In order for the core application 128 to perform the functions/algorithms described herein, the core application 128 may need access to the data stored within the proprietary database 124. A proprietary data manager 130 may be implemented between the core application 128 and the proprietary database 124. The proprietary data manager 130 controls access to the proprietary database 124, thereby ensuring that access to the proprietary database 124 is authorized. The proprietary data manager 130 utilizes meta-data defined by the core application 128 to map customer proprietary data to a common data model used by a rules engine in executing any rules or program logic in the core application. This allows the proprietary data manager 130 to be separated from the environment where the rules operate (i.e., within the core application 130). The purpose of the proprietary data manager 130 is to deliver data to the core application 130 (i.e., rules engine) in a manner that allows the core application 130 to be isolated from the proprietary database 124 where proprietary records are stored. This architecture improves performance of the system and enhances security of the proprietary data and functionality.

For example, the proprietary data manager 130 receives an event from the core application 128 requesting an analysis to be performed on a record contained within the proprietary database 124. The proprietary data manager 130 thereafter retrieves the requested record from the proprietary database 124 and attaches historical records required to perform analysis according to the received event. The retrieved requested record and attached historical records are packaged into a buffer and sent to the core application 130 for further processing. This allows a variety of storage technologies to be utilized by the local execution environment 122 by providing a data mapping "driver" for the different environments. For example, data could be stored/retrieved from a relational database, from a document based storage system, or a large distributed storage technology such as HADOOP, which is an open-source software framework for storing data and running applications.

The proprietary database 124 includes healthcare data such as clinical data, claims data, socio-demographic data, and case management data, for example. However, the proprietary database 124 may contain other data not described herein. Moreover, the proprietary database 124 may contain structuring sufficient to perform the processes/functions described herein. For example, data within the proprietary database 124 may be structured according to meta-data definitions that map data according to various data models.

The configuration capsule(s) 110 control the user interface 126, the core application 128, and the proprietary data manager 130 as described herein below.

Figure 2:
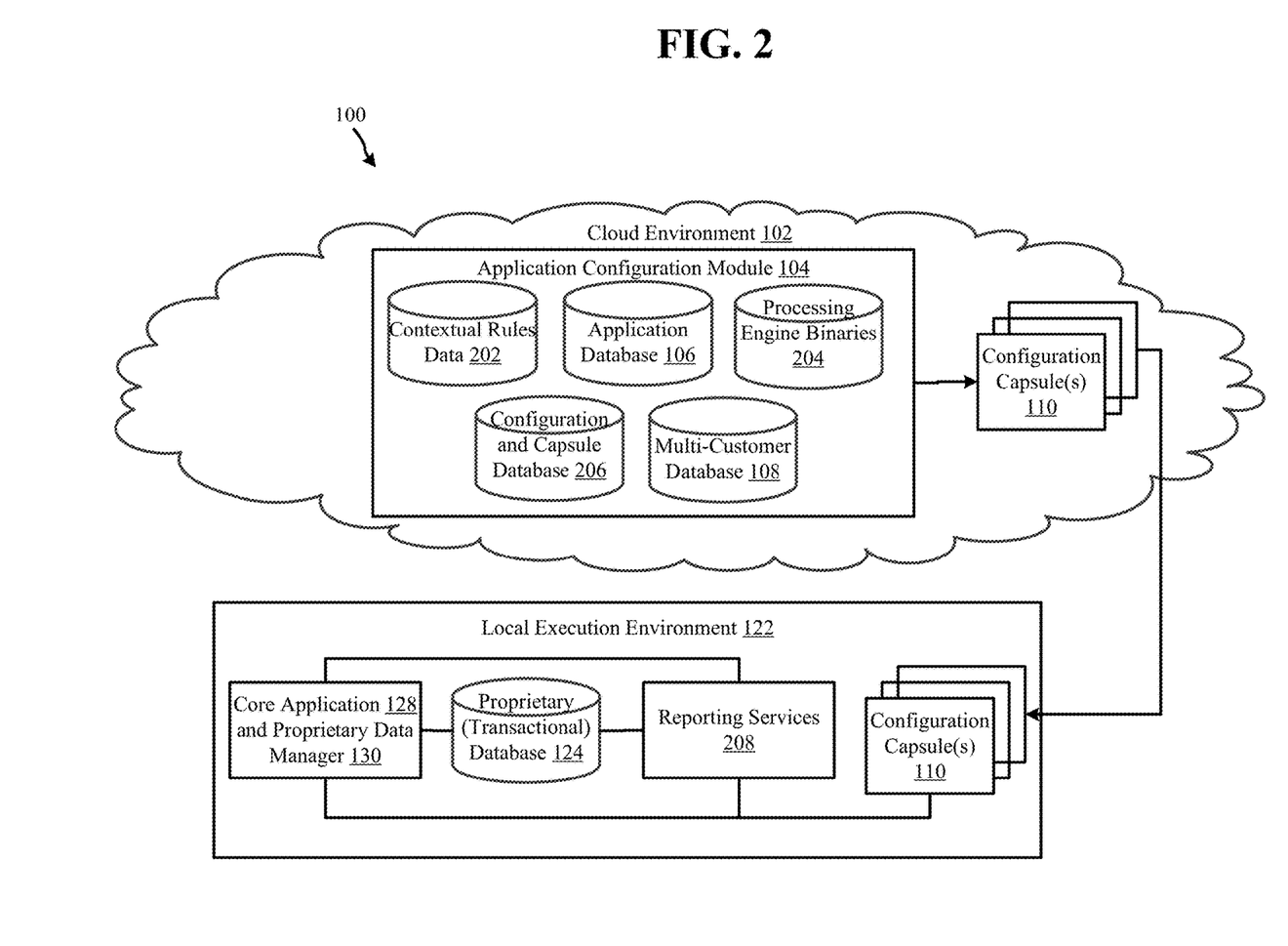
FIG. 2 illustrates configuration and application of a configuration capsule for use within the specially configured cloud-hybrid system for secure processing and maintaining proprietary or sensitive data according to the present disclosure.

Attention is now given to FIG. 2, which illustrates configuration and application of the configuration capsule 110 within the cloud-hybrid system 100. The application configuration module 104 of the cloud environment 102 includes contextual rules data 202, the application database 106, processing engine binaries 204, a configuration and capsule database 206, and the multi-customer database 108. The contextual rules data 202 is an application creator created knowledge base of data required to support rule execution. The application database 106 is an application creator created pre-built rules library. The library contains the rules applicable to execution of the application without customer configuration. The processing engine binaries 204 are versioned rule engine binaries used to execute customer and application creator created rules/logic stored within the multi-customer and application databases 106, 108, respectively. The configuration and capsule database 206 stores previously generated configuration capsule data. The multi-customer database 108 contains customized configuration rules/logic generated by multiple customers. Each configuration capsule generated contains data from some or all of the data storages 202, 106, 204, 206, 108. Configuring the cloud environment 102 according to the aforementioned structures and storages allows for customer self-configuration, application creator configuration tailored to the application generally, consulting analysis and optimization by the application creator, as well as product issue and configuration support.

The configuration of the cloud-hybrid system 100 described herein allows the application creator to conduct support on stored configurations without intrusive investigation into local execution environment 122 processing and data. The configuration of the cloud-hybrid system 100 also allows for the application creator to push customized configuration capsules 110 from the cloud environment 102 to the local execution environments 122 of several customers at once. Furthermore, configuration of the cloud-hybrid system 100 as described herein allows for traceable development and testing of new configurations and rules in the cloud environment 102 without disturbing processing within the local execution environment 122.

The configuration capsule 110 is pushed or pulled to the local execution environment 122. Delivery of the configuration capsule 110 may involve the use of unsecure and secure Internet and intra-net pathways. As such, the configuration capsule 110 may be encrypted using means known in the art prior to the configuration capsule 110 leaving the cloud environment. The local execution environment 122 includes the core application 128 and proprietary data manager 130, the proprietary (transaction database 124, and reporting services 208. Portions of the configuration capsule 100 are executable by the core application 128, proprietary data manager 130, and the reporting services to perform healthcare claims processing and reporting, among other healthcare processing and functioning.

Configuration of the local execution environment 122 described herein allows for customer system and local user management, as well as customer transaction processing and reporting. By maintaining configuration data and processes in the cloud environment 102, susceptibility of proprietary and sensitive resources of the local execution environment 122 is greatly diminished if the configuration data is subject to unauthorized access. Further, maintaining the configuration data and processes in the cloud environment 102 allows for the customer to control when configuration capsules 110 are deployed, resulting in greater efficiency of application updates and decreased inhibition of customer processes due to the updates. Additionally, separation of the system 100 into a cloud environment 102 and a local execution environment 122 means loss of transactional data in the local execution environment 122 does not automatically result in loss of configuration preferences.

Figure 3:
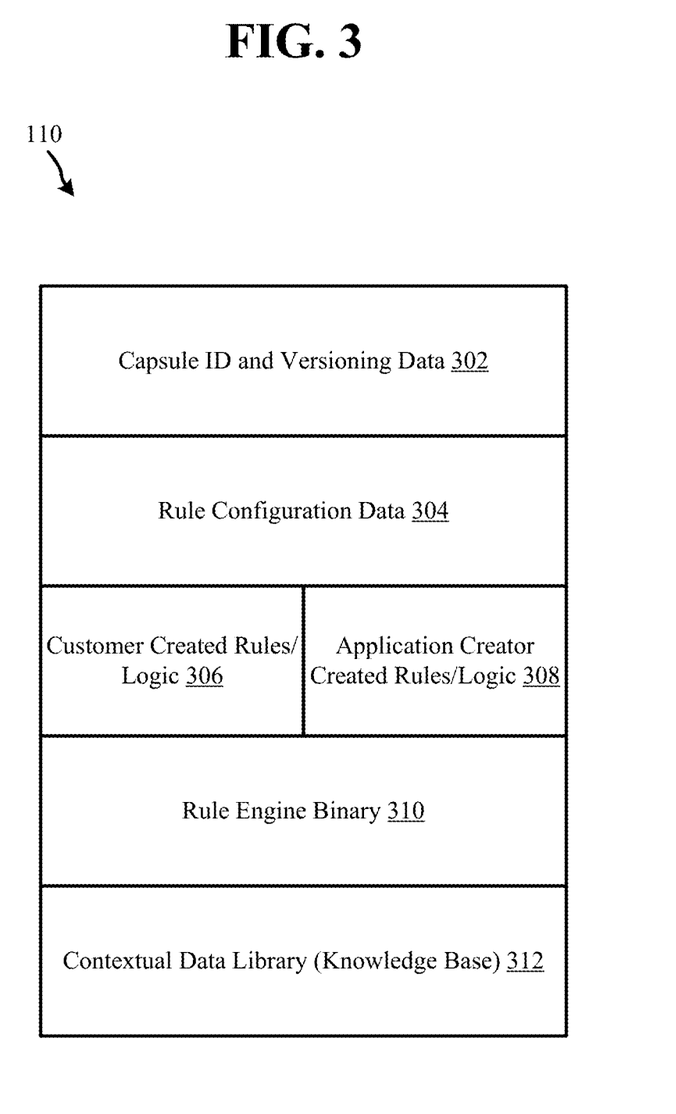
FIG. 3 illustrates a structure of a configuration capsule for use within the specially configured cloud-hybrid system for secure processing and maintaining proprietary or sensitive data according to the present disclosure.

Referring now to FIG. 3, a data structure of the configuration capsule 110 is described. Each configuration capsule 110 includes capsule ID and versioning data 302, rule configuration data 304, customer created rules/logic 306, application creator created rules/logic 308, rule engine binary 310, and a contextual data library 312. The capsule ID and versioning data 302 identifies the configuration capsule 110, and describes content versions and source/destination information. The source/destination information may include customer network identifying information or specific computer identifying information. The rule configuration data 304 defines which rules of n rules are enabled, parameters and constraints on the enabled rules execution, and dependencies. The customer created rules/logic 306 are customer created configuration rules/logic unique to implementation of the application in the customer's local environment. The application creator created rules/logic 308 are application creator created rules/logic available for use by the customer through application licensing. The rule engine binary 310 are versioned rule engine binaries used to execute the customer and application creator created rules/logic 306, 308. The contextual data library 312 is an application creator created knowledge base of data required to support rule execution.

Figure 4:
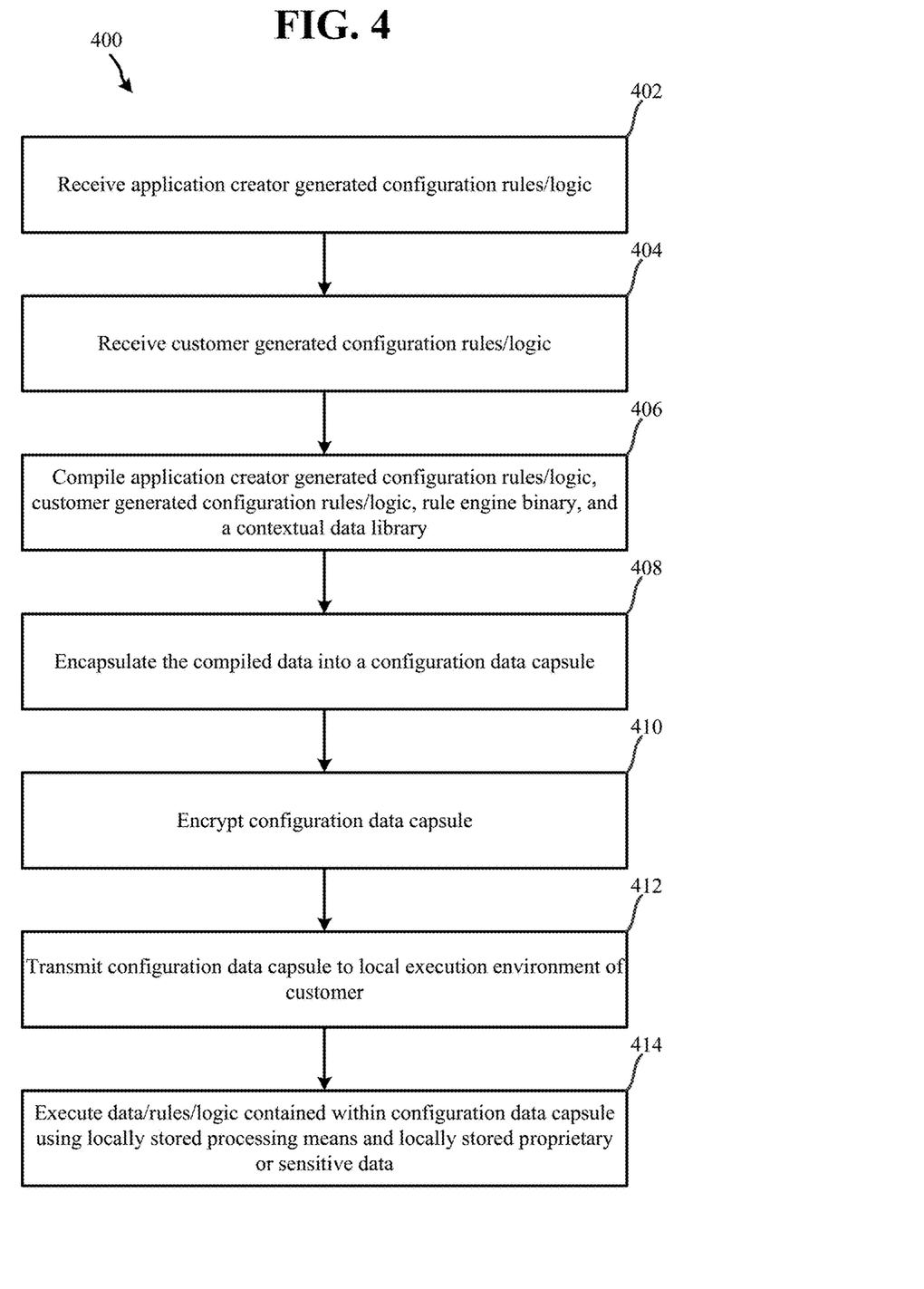
FIG. 4 is a process flow diagram illustrating a method for generating and implementing a configuration capsule for use within the specially configured cloud-hybrid system for secure processing and maintaining proprietary or sensitive data according to the present disclosure.

Attention is now given to FIG. 4, which illustrates a method 400 for generating and implementing a configuration capsule 110 according to the present disclosure. At block 402 application creator generated configuration rules/logic for general configuration of the application are received in a cloud environment. At block 404 customer generated configuration rules/logic for configuration specific to the customer's local execution environment are received in the cloud environment. The application creator and customer generated configuration rules/logic, rule engine binary, and a contextual data library are compiled (illustrated as block 406) and encapsulated into a configuration data capsule (illustrated as block 408). At block 410 the configuration data capsule is optionally encrypted using means known in the art. After encapsulation (illustrated as block 408) and optional encryption (illustrated as block 410), the configuration data capsule is transmitted to the local execution environment of the customer or provided the configuration rules/logic (illustrated as block 412). Thereafter, at block 414, the data/rules/logic contained within the configuration data capsule are executed by locally stored processing means and locally stored proprietary or sensitive data.

Although aspects of the present disclosure are described with respect to examples in a health care data environment, it should be understood that various disclosed techniques can be used in numerous other fields of technology in which cloud based services are used to provide substantial improvements in these fields. Various applications of the disclosed techniques such as Cloud-Hybrid Application Deployment and Cloud managed configuration and content customization provide substantial improvements to the functioning of the computer apparatus and the technical environments in which the various applications are implemented.

Moreover, although the present disclosure has been described herein with reference to the accompanying drawings, it is to be understood that the present disclosure is not limited to those precise teachings, and that various other changes and modifications may be made by one skilled in the art without departing from the spirit and scope of the present disclosure.

What is claimed is:

1. A cloud-hybrid data processing system for processing and managing proprietary data in a hybrid environment, the cloud-hybrid system comprising:
a cloud environment including generalized application data and customer provided application configuration data, the application data governing general configuration of an application and how the application processes material; and
a local computing environment in communication with the cloud computing environment, the local computing environment including a computing device and storing sensitive data;
a configuration capsule received by the local computing environment from the cloud environment, the configuration capsule including:
configuration capsule ID and versioning data;
the customer provided application configuration data; and
the generalized application data, the generalized application data being application creator provided, the generalized application data including:
rule configuration data;
generalized application configuration data;
rules engine binary; and
a contextual data library;
wherein the configuration capsule is configured to define and support customized rule behavior, based on the customer provided application configuration data and the generalized application data, by the application to facilitate system security of at least the sensitive data; and
the configuration capsule is further configured to be updated in the cloud computing environment based on updated customer provided application configuration data and updated generalized application data.

2. The system of claim 1, wherein the cloud environment includes user interface configuration data implementable within the local computing environment.

3. The system of claim 1, wherein the local computing environment includes a proprietary data manager configured to control access by the application to the sensitive data.

4. The system of claim 1, wherein the contextual data library is a knowledge base of data used to support rule execution by the application.

5. The system of claim 1, wherein previous configuration capsule data is stored within the cloud environment, the previous configuration data corresponding to configuration capsules previously implemented within the local computing environment.

6. The system of claim 1, wherein configuration capsules may be transmitted from the cloud environment to customer local computing environments at once, each of the configuration capsules containing unique configuration data specific to the customer that receives the configuration capsule.

7. The system of claim 1, wherein the application performs at least one of clinical content editing or analysis of structural correctness of data transmissions according to data stored within the configuration capsule.

8. A method for processing and managing proprietary data in a hybrid cloud and local computing environment, comprising the steps of:
receiving, by a cloud environment, application creator and customer generated configuration data;
creating, by the cloud environment, a configuration capsule, the configuration capsule including the application creator and customer generated configuration data, and being configured to define and support customized rule behavior, based on the customer provided application configuration data and the generalized application data, by the application to facilitate system security; and
transmitting, by the cloud environment, the configuration capsule to a local computing environment, the configuration capsule being executable within the local computing environment to facilitate security of locally stored sensitive data;
updating, by the cloud environment, the configuration capsule based on updated customer provided application configuration data and updated generalized application data.

9. The method of claim 8, wherein creating the configuration capsule includes compiling rule engine binary and a contextual data library, the rule engine binary and contextual data library being created by the application creator.

10. The method of claim 8, wherein receiving the configuration data includes receiving, by the cloud environment, application creator generated user interface configuration data.

11. The method of claim 8, further comprising the step of:
encrypting, by the cloud environment, the configuration capsule prior to transmitting the configuration capsule to the local computing environment.

12. The method of claim 8, wherein transmitting the configuration capsule includes use of the Internet.

13. The method of claim 8, wherein the configuration capsule data is executed to perform at least one of clinical content editing or analysis of structural correctness of data transmissions.

14. The method of claim 8, further comprising the step of:
storing, by the cloud environment, previously generated configuration capsule data, the previously generated configuration capsule data being previously transmitted to the local computing environment.

15. An apparatus for processing and managing proprietary data for security of said proprietary data, comprising:
a processor; and
a memory device including instructions operable to be executed by the processor to perform a set of actions, configuring the processor to:
receive a configuration capsule from a cloud environment, the configuration capsule including application creator and customer generated configuration data, and being configured to define and support customized rule behavior, based on the application creator and customer generated configuration data, by the application to facilitate system security;
execute rules within the configuration capsule to perform at least one of content editing or analysis of structural correctness of data transmissions by accessing sensitive data locally stored in a database; and
update the configuration capsule in the cloud environment based on updated customer provided application configuration data and updated generalized application data.

16. The apparatus of claim 15, wherein receiving the configuration capsule includes receiving the configuration capsule via the Internet.

17. The apparatus of claim 15, wherein the processor is further configured to:
retrieve a previously generated configuration capsule from the cloud environment, the previously generated configuration capsule being previously received but no longer stored by the apparatus.

18. The apparatus of claim 15, wherein the processor is further configured to:
   generate a user interface using rules stored within the received configuration capsule, the rules being application creator generated.

19. The apparatus of claim 15, wherein the processor is further configured to:
   control access by an application to the locally stored sensitive data by using rules stored within the configuration capsule.

20. The apparatus of claim 15, wherein the configuration capsule includes rule engine binary and a contextual data library, the rule engine binary and contextual data library being application creator generated.

* * * * *